(12) United States Patent
Kitamura

(10) Patent No.: US 7,983,390 B2
(45) Date of Patent: Jul. 19, 2011

(54) ENERGY SUBTRACTION PROCESSING APPARATUS, METHOD, AND RADIATION IMAGE DIAGNOSIS SYSTEM

(75) Inventor: Yoshiro Kitamura, Tokyo (JP)

(73) Assignee: Fujifilm Corporation, Tokyo (JP)

( * ) Notice: Subject to any disclaimer, the term of this patent is extended or adjusted under 35 U.S.C. 154(b) by 198 days.

(21) Appl. No.: 12/457,825

(22) Filed: Jun. 23, 2009

(65) Prior Publication Data

US 2009/0323896 A1    Dec. 31, 2009

(30) Foreign Application Priority Data

Jun. 25, 2008  (JP) ................................ 2008-165760

(51) Int. Cl.
*H05G 1/64*  (2006.01)
(52) U.S. Cl. ..................................... 378/98.12; 378/155
(58) Field of Classification Search ............... 378/98.9, 378/98.11, 98.12, 62, 154–155
See application file for complete search history.

(56) References Cited

U.S. PATENT DOCUMENTS

| 6,244,507 B1 * | 6/2001 | Garland et al. ............... 235/383 |
| 6,624,439 B1 | 9/2003 | Arakawa |
| 2002/0126800 A1 * | 9/2002 | Matsumoto et al. .......... 378/154 |
| 2008/0080673 A1 * | 4/2008 | Yamakita ...................... 378/155 |

* cited by examiner

*Primary Examiner* — Hoon Song
(74) *Attorney, Agent, or Firm* — Jean C. Edwards, Esq.; Edwards Neils PLLC

(57) ABSTRACT

In energy subtraction processing, grid information representing grid use conditions at the time of imaging operations for a plurality of radiation images of an object is acquired. Weight factors are adjusted in accordance with the grid information, which has been acquired. A weighted addition or subtraction process is performed on corresponding pixels in the plurality of the radiation images of the object by use of the weight factors, which have thus been adjusted. A constituent image representing a predetermined constituent in the object is thus formed.

6 Claims, 11 Drawing Sheets

| ENERGY DISTRIBUTION | | GRID INFORMATION | CONSTITUENT TO BE SEPARATED | WEIGHT FACTOR |
| --- | --- | --- | --- | --- |
| LOW-ENERGY | HIGH-ENERGY | | | |
| $V_1$ | $V_2$ | NONE | SOFT TISSUE | $W_1$ |
| $V_1$ | $V_2$ | NONE | BONE | $W_2$ |
| $V_1$ | $V_2$ | $G_1$ | SOFT TISSUE | $W_3$ |
| $V_1$ | $V_2$ | $G_1$ | BONE | $W_4$ |
| $V_1$ | $V_2$ | $G_2$ | SOFT TISSUE | $W_5$ |
| $V_1$ | $V_2$ | $G_2$ | BONE | $W_6$ |
| $V_3$ | $V_4$ | $G_3$ | SOFT TISSUE | $W_7$ |
| $V_3$ | $V_4$ | $G_3$ | BONE | $W_8$ |
| ⋮ | ⋮ | ⋮ | ⋮ | ⋮ |

FIG.11

| OBJECT SITE IMAGED | TUBE VOLTAGE FOR ORDINARY DIAGNOSIS | TUBE VOLTAGE FOR ENERGY SUBTRACTION PROCESSING | GRID INFORMATION |
|---|---|---|---|
| CHEST | 100~140kVp | 60~80kVp | GRID USED, HIGH GRID RATIO (10:1) |
| ABDOMEN | 60~80kVp | 120~140kVp | GRID USED, LOW GRID RATIO (6:1) |
| LIMB | 40~60kVp | 100~120kVp | NONE |

SPECTRAL DISTRIBUTION OF INCIDENT X-RAYS

SPECTRAL DISTRIBUTION VERSUS ATTENUATION COEFFICIENT

ENERGY SUBTRACTION PROCESSING APPARATUS, METHOD, AND RADIATION IMAGE DIAGNOSIS SYSTEM

CROSS-REFERENCE TO RELATED APPLICATIONS

The present application claims priority from Japanese Patent Application No. 2008-165760, filed Jun. 25, 2008, the contents of which are herein incorporated by reference in their entirety.

BACKGROUND OF THE INVENTION

1. Field of the Invention

This invention relates to an energy subtraction processing technique, wherein a plurality of radiation images having been formed respectively with a plurality of kinds of radiation having different energy distributions are obtained, and wherein a specific image constituent embedded in the radiation images is separated by use of the obtained radiation images.

2. Description of the Related Art

Techniques for performing energy subtraction processing have heretofore been known in the field of medical image processing. With the energy subtraction processing techniques, a plurality of radiation images carrying image information of a single object are formed with a plurality of kinds of radiation having different energy distributions. Thereafter, image signal components of image signals representing the plurality of the radiation images, which image signal components represent corresponding pixels in the radiation images, are multiplied by appropriate weight factors, and the thus weighted image signal components are subjected to a subtraction process. From the subtraction process, a difference signal, which represents only the image of a specific structure of the object, is obtained. By the utilization of the energy subtraction processing techniques, it is possible to form a soft tissue image, in which a bone constituent has been removed from the input images, and a bone image, in which a soft tissue constituent has been removed from the input images. Therefore, image reading may be performed on the image, in which the area other than the area to be diagnosed has been removed, and the perceptibility of the area to be diagnosed in the image is enhanced. (Reference may be made to, for example, U.S. Pat. No. 6,624,439.)

FIG. 12 is an explanatory view showing a scattered radiation removing effect of a grid. As illustrated in FIG. 12, at the time at which the radiation having been irradiated from a radiation source passes through an object, the radiation attenuates due to two effects, i.e. a photoelectric effect and a Compton effect. Part of the radiation having attenuated due to the Compton effect undergoes a change in direction of travel and constitutes scattered ray components. The scattered ray components cause the level of contrast of the radiation image to become low. Therefore, a grid is located between the object and a detector for detecting the radiation image information of the object, and the scattered ray components are thereby suppressed at the time of an imaging operation.

The energy subtraction processing apparatus disclosed in U.S. Pat. No. 6,624,439 is provided with an imaging system in which a grid is located. With the disclosed energy subtraction processing apparatus, energy subtraction processing is performed by use of radiation images having been formed with the radiation, from which the scattered ray components have been removed by the grid.

As radiation imaging apparatuses utilizing flat panel detectors have become popular in recent years, it is becoming possible to perform the imaging operations for energy subtraction processing with respect to various object sites to be imaged. At the time of the imaging operations described above, a tube voltage and grid use conditions, such as the presence or absence of the grid and the kind of the grid, are adjusted in accordance with the object sites to be imaged.

However, in the cases of the conventional energy subtraction processing as described in, for example, U.S. Pat. No. 6,624,439, wherein the object site to be processed is limited, the grid use conditions at the time of the imaging operations are set fixedly, and therefore it has not been necessary for an effect of a difference in grid use conditions upon the energy subtraction processing to be taken into consideration in the energy subtraction processing.

SUMMARY OF THE INVENTION

The primary object of the present invention is to provide an energy subtraction processing apparatus, which performs more accurate energy subtraction processing in accordance with grid use conditions at the time of imaging operations.

Another object of the present invention is to provide an energy subtraction processing method, which performs more accurate energy subtraction processing in accordance with grid use conditions at the time of imaging operations.

A further object of the present invention is to provide a radiation image diagnosis system for carrying out the energy subtraction processing method.

The present invention provides an energy subtraction processing apparatus, comprising constituent image forming means for:

receiving input of a plurality of radiation images having been formed with radiation carrying image information of an object, each of the radiation images representing degrees of transit attenuation of one of a plurality of patterns of radiation having different energy distributions, which transit attenuation occurs in the object, performing a weighted addition or subtraction process on corresponding pixels in the plurality of the radiation images by use of given weight factors, and thereby forming a constituent image representing a predetermined constituent in the object, wherein the apparatus further comprises:

grid information acquiring means for acquiring grid information representing grid use conditions at the time of the imaging operations for the plurality of the radiation images, and weight factor adjusting means for adjusting the weight factors in accordance with the grid information, which has been acquired by the grid information acquiring means, the constituent image forming means performing the weighted addition or subtraction process by use of the weight factors, which have been adjusted by the weight factor adjusting means.

The present invention also provides an energy subtraction processing method, comprising a constituent image forming step of:

receiving input of a plurality of radiation images having been formed with radiation carrying image information of an object, each of the radiation images representing degrees of transit attenuation of one of a plurality of patterns of radiation having different energy distributions, which transit attenuation occurs in the object, performing a weighted addition or subtraction process on corresponding pixels in the plurality of the radiation images by use of given weight factors, and thereby forming a constituent image representing a predetermined constituent in the object, wherein the method further comprises:

a grid information acquiring step of acquiring grid information representing grid use conditions at the time of the imaging operations for the plurality of the radiation images, and a weight factor adjusting step of adjusting the weight factors in accordance with the grid information, which has been acquired, the constituent image forming step being the step of performing the weighted addition or subtraction process by use of the weight factors, which have been adjusted by the weight factor adjusting step.

The energy subtraction processing method in accordance with the present invention may be furnished in the form of a computer readable recording medium, on which an energy subtraction processing computer program for causing a computer to execute the energy subtraction processing method in accordance with the present invention has been recorded and from which the computer is capable of reading the program.

The present invention still further provides a radiation image diagnosis system, comprising:

i) radiation irradiating means for irradiating radiation having a predetermined energy distribution to an object, ii) radiation detecting means for detecting the irradiated radiation, iii) conversion means for converting the detected radiation into a digital image signal and thereby forming the digital image signal representing a radiation image of the object, and iv) constituent image forming means for:

receiving input of a plurality of digital image signals, each of which has been formed by the conversion means and represents one of a plurality of radiation images having been formed with radiation carrying image information of an object, each of the radiation images representing degrees of transit attenuation of one of a plurality of patterns of radiation having different energy distributions, which transit attenuation occurs in the object, performing a weighted addition or subtraction process on corresponding pixels in the plurality of the radiation images by use of given weight factors, and thereby forming a constituent image representing a predetermined constituent in the object, wherein the system is constituted such that a given grid may be located between the object and the radiation detecting means, and the system further comprises:

grid information acquiring means for acquiring grid information representing grid use conditions at the time of the imaging operations for the plurality of the radiation images, and weight factor adjusting means for adjusting the weight factors in accordance with the grid information, which has been acquired by the grid information acquiring means, the constituent image forming means performing the weighted addition or subtraction process by use of the weight factors, which have been adjusted by the weight factor adjusting means.

The effect of a difference in grid use conditions upon the energy subtraction processing will be described hereinbelow by taking the energy subtraction processing, in which two radiation images are inputted, as an example.

A radiation dose I detected by the radiation detecting means may be represented by Formula (1) shown below:

$$I = \int A(E) \times \exp(-\mu(E) \times t) \times B(E) dE \quad (1)$$

wherein $A(E)$ represents the input spectrum, $\mu(E)$ represents the radiation attenuation coefficient of the object, t represents the thickness of the object, and $B(E)$ represents the absorption coefficient of the radiation detecting means.

The radiation attenuation coefficient $\mu(E)$ depends upon the spectral distribution of the incident radiation and the atomic number of the tissue constituting the object. Ordinarily, as the tube voltage of the radiation producing device becomes high, the value of $\mu$ becomes small. Also, as the atomic number of the tissue constituting the object becomes high, the value of $\mu$ becomes large. FIG. 13 is a graph showing examples of spectral distributions of two kinds of radiation having different energy distributions (low-energy radiation and high-energy radiation). FIG. 14 is a graph showing examples of relationships between radiation attenuation coefficients of a bone and a soft tissue of a human body and a tube voltage of a radiation producing device. In this case, the atomic number of the constituent element of the bone is larger than the atomic number of the constituent element of the soft tissue.

Also, the value obtained from integration of the radiation attenuation coefficient in accordance with the spectral distribution illustrated in FIG. 14 represents the effective attenuation coefficient taking an average of the entire spectral distribution.

In accordance with Formula (1), the logarithmic radiation exposure dose E at each of the pixel positions in the radiation image may be approximately represented by Formula (2) shown below by use of the radiation attenuation coefficient $\mu$ and the total dose Const of the irradiated radiation.

$$E = -\mu \times t + Const \quad (2)$$

In cases where Const-E is replaced by E', a simpler formula may be obtained as Formula (3) shown below.

$$E' = P \times t \quad (3)$$

In cases where the object is constituted of two different tissues respectively having the radiation attenuation coefficients $\mu_1$ and $\mu_2$, Formula (3) may be deformed into Formula (4) shown below:

$$E' = \mu_1 \times t1 + \mu_2 \times t2 \quad (4)$$

wherein t1 represents the thickness of the tissue having the radiation attenuation coefficient $\mu_1$, and t2 represents the thickness of the tissue having the radiation attenuation coefficient $\mu_2$.

In cases where Formula (4) is used, the two radiation images, each of which represents the degrees of transit attenuation of one of the plurality of patterns of radiation having different energy distributions, the transit attenuation occurring in the object, are expressed as Formulas (5) and (6) shown below.

$$E_L = \mu_{1L} \times t1 + \mu_{2L} \times t2 \quad (5)$$

$$E_H = \mu_{1H} \times t1 + \mu_{2H} \times t2 \quad (6)$$

The suffix L as used herein represents, of the two radiation images, the image (hereinbelow referred to as the low-energy image) representing the degrees of transit attenuation of the radiation having the energy distribution on the lower-energy side. Also, the suffix H as used herein represents the image (hereinbelow referred to as the high-energy image) representing the degrees of transit attenuation of the radiation having the energy distribution on the higher-energy side.

The energy subtraction processing is the processing, wherein a weighted subtraction process is performed on the two radiation images represented respectively by Formulas (5) and (6), wherein the coefficient part of each term representing the constituent other than the constituent, which is to be separated, in the right side of each of the formulas shown above is set to be 0, and wherein a relation, which does not depend upon the thickness of the constituent other than the constituent to be separated, is thereby obtained.

In cases where the weight factor with respect to the radiation image $E_L$ is represented by $w_L$, and the weight factor with respect to the radiation image $E_H$ is represented by $w_H$, the weighted subtraction process may be represented by Formula (7) shown below.

$$w_L \times E_L - w_H \times E_H = (w_L \times \mu_{1L} - w_H \times \mu_{1H}) \times t1 + (w_L \times \mu_{2L} - w_H \times \mu_{2H}) \times t2 \quad (7)$$

In cases where the image, from which the pattern of the tissue having the thickness t1 has been removed, is to be formed with Formula (7), it is necessary that the coefficient part with respect to t1 is set to be equal to 0, i.e., $w_L \times \mu_{1L} - w_H \times \mu_{1H} = 0$. Therefore, Formula (8) shown below obtains.

$$w_L / w_H = \mu_{1H} / \mu_{1L} \quad (8)$$

Also, if $w_L$ is set to be equal to 1, $w_H$ may be represented by Formula (9) shown below.

$$w_H = \mu_{1L} / \mu_{1H} \quad (9)$$

In cases where the image, from which the pattern of the tissue having the thickness t2 has been removed, is to be formed with Formula (7), it is necessary that the coefficient part with respect to t2 is set to be equal to 0, i.e., $w_L \times \mu_{2L} - w_H \times \mu_{2H} = 0$. Therefore, Formula (10) shown below obtains.

$$w_L / w_H = \mu_{2H} / \mu_{2L} \quad (10)$$

Also, if $w_L$ is set to be equal to 1, $w_H$ may be represented by Formula (11) shown below.

$$w_H = \mu_{2L} / \mu_{2H} \quad (11)$$

As described above, in the cases of the energy subtraction processing performed on the two radiation images, each of the weight factors $w_L$ and $w_H$ may be expressed as the ratio between the radiation attenuation coefficients of the constituent (i.e., the constituent to be removed) other than the constituent, for which the constituent image is to be formed, between the constituents in the original radiation images.

The logarithmic exposure dose E of the radiation image is the value obtained from logarithmic conversion of the radiation dose, which has passed through the object at the time of the imaging operation performed on the object and has been irradiated to the radiation detecting means. The exposure dose is capable of being obtained from direct detection of the radiation irradiated to the radiation detecting means. However, it is not always possible to detect the exposure dose with respect to each of the pixels in the radiation image. However, as the exposure dose becomes large, the pixel value of each of the pixels in the image obtained by the radiation detecting means becomes large. Therefore, the pixel value and the exposure dose have the correspondence relationship. Accordingly, the exposure dose in each of the formulas shown above may be replaced by the pixel value.

The radiation detected by the radiation detecting means at the time of the imaging operation contains the scattered ray components. Therefore, the level of contrast of the radiation image becomes low, depending upon the quantity of the scattered ray components. However, in cases where the grid is utilized at the time of the imaging operation, the quantity of the radiation detected by the radiation detecting means becomes small due to the scattered ray removing effect of the grid. Also, the extent of the scattered ray removing effect varies in accordance with the kind of the grid used, and therefore the extent of the decrease in quantity of radiation detected by the radiation detecting means varies in accordance with the kind of the grid used. As described above, the apparent radiation attenuation characteristics alter in accordance with the grid use conditions at the time of the imaging operation. In accordance with the alteration of the apparent radiation attenuation characteristics, the weight factors in the energy subtraction processing alter as shown above in Formulas (8) and (10).

In view of the effect of the difference in grid use conditions upon the weight factors in the energy subtraction processing, the present invention is characterized by the adjustment of the weight factors in the energy subtraction processing in accordance with the grid use conditions.

The present invention will hereinbelow be illustrated in more detail.

The term "grid information" as used herein means the information, which represents whether the grid is used or is not used at the time of the imaging operation, and the information, which represents the kind of the grid used at the time of the imaging operation. Examples of the kinds of the grids include the grid ratio, the grid density, the grid pattern (a linear grid, a cross grid), and the grid material. The term "grid ratio" as used herein means the relative height of the absorption foils of the grid with a spacing of the absorption foils being taken as being 1 (i.e., means the value of h/D in the grid sectional view shown in FIG. 15). Also, the term "grid density" as used herein means the number of the absorption foils of the grid per unit length (i.e., means the value of 1/(d+D) in the grid sectional view shown in FIG. 15). The grid may be a stationary grid. Alternatively, the grid may be a movable grid.

As described above, the weight factors are adjusted in accordance with the grid information. The adjustment of the weight factors may be performed in the manner described below. Specifically, the relationship between the grid information and the weight factors may be obtained previously with experiments and statistics. Reference information representing the correspondence relationship between the grid information and the weight factors may thus be prepared previously. Reference may then be made to the reference information in accordance with the grid information having been acquired by the grid information acquiring means. The information representing the weight factors having the correspondence relationship with the acquired grid information may thus be acquired.

Examples of the relationships between the grid information and the weight factors include the relationship, such that an increase rate of an absolute value of the weight factor for a high-energy image among the plurality of the radiation images, which absolute value is set in cases where the grid is used at the time of the imaging operation, with respect to the absolute value of the weight factor for the high-energy image among the plurality of the radiation images, which absolute value is set in cases where the grid is not used at the time of the imaging operation, is higher than the increase rate of the absolute value of the weight factor for a low-energy image among the plurality of the radiation images, which absolute value is set in cases where the grid is used at the time of the imaging operation, with respect to the absolute value of the weight factor for the low-energy image among the plurality of the radiation images, which absolute value is set in cases where the grid is not used at the time of the imaging operation. Examples of the relationships between the grid information and the weight factors also include the relationship, such that an increase rate of an absolute value of the weight factor for a high-energy image among the plurality of the radiation images, which increase rate accompanies an increase of the grid ratio, is higher than the increase rate of the absolute value of the weight factor for a low-energy image among the plurality of the radiation images, which increase rate accompanies the increase of the grid ratio.

Examples of the radiation detecting means include a flat panel detector (FPD) utilizing a CMOS, or the like, and a stimulable phosphor sheet. The radiation detecting means may be selected appropriately in accordance with the imaging technique employed.

The plurality of the radiation images having been formed with the radiation carrying the image information of the object, each of the radiation images representing the degrees of transit attenuation of one of the plurality of patterns of radiation having different energy distributions, which transit attenuation occurs in the object, may be obtained with a multi-shot energy subtraction processing technique, wherein the imaging operations are performed multiple times by use of the plurality of patterns of radiation having different energy distributions. Alternatively, the plurality of the radiation images having been formed with the radiation carrying the image information of the object, each of the radiation images representing the degrees of transit attenuation of one of the plurality of patterns of radiation having different energy distributions, which transit attenuation occurs in the object, may be obtained with a one-shot energy subtraction processing technique, wherein radiation is irradiated one time to a plurality of radiation detecting means superposed one upon another with an additional filter, such as an energy separation filter, intervening between adjacent radiation detecting means, wherein the energy distribution of the radiation carrying the image information of the object is thus altered with one time of the irradiation, and wherein the plurality of patterns of radiation having different energy distributions are detected respectively by the plurality of the radiation detecting means.

In accordance with the present invention, at the time of the energy subtraction processing for performing the weighted addition or subtraction process on corresponding pixels in the plurality of the radiation images by use of the given weight factors, the grid information representing the grid use conditions at the time of the imaging operations for the plurality of the radiation images is acquired, and the weight factors are adjusted in accordance with the acquired grid information. Therefore, the weight factors are adjusted such that the weight factors accurately reflect the grid use conditions at the time of the imaging operations. The weighted addition or subtraction process is performed by use of the thus adjusted weight factors, and therefore the constituent image is obtained accurately.

BRIEF DESCRIPTION OF THE DRAWINGS

FIG. 11 is a table showing examples of relationships among an object site to be imaged, a tube voltage, and grid information.

DESCRIPTION OF THE PREFERRED EMBODIMENTS

The present invention will hereinbelow be described in further detail with reference to the accompanying drawings.

As an embodiment of the radiation image diagnosis system in accordance with the present invention, an X-ray image diagnosis system will be described hereinbelow. With the embodiment of the X-ray image diagnosis system, two patterns of X-rays having different energy distributions are irradiated successively to the chest of a human body, and two X-ray images are thereby formed. Also, the energy subtraction processing is performed on the two X-ray images, and a constituent image representing a soft tissue constituent and a constituent image representing a bone constituent are thereby formed. The thus obtained constituent images are displayed together with a diagnostic image.

Figure 1:
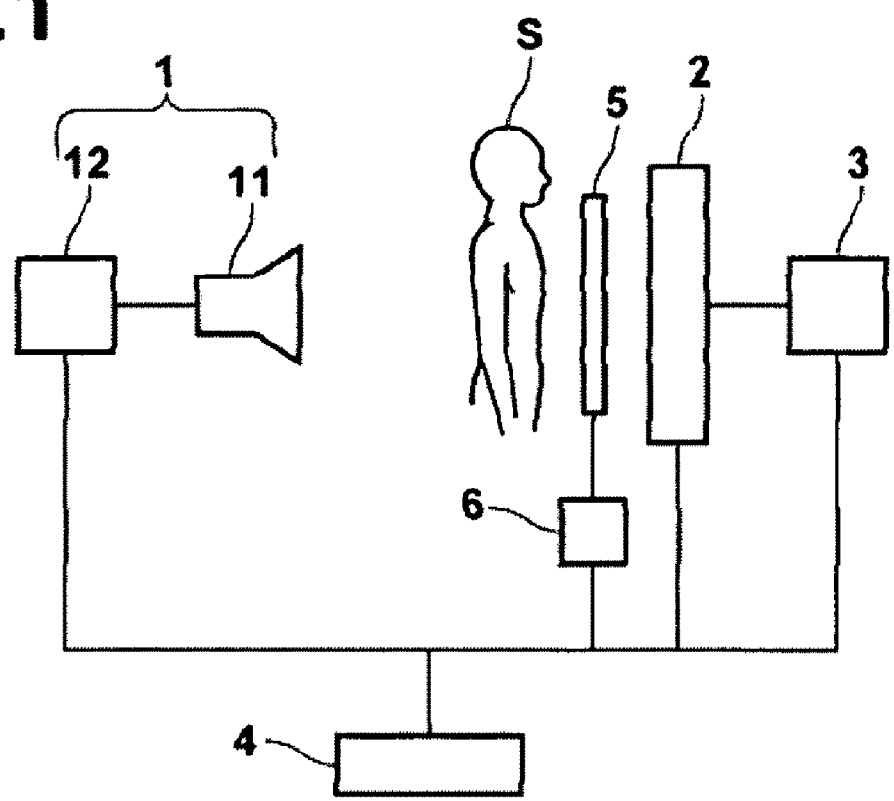
FIG. 1 is an explanatory view showing an embodiment of an X-ray image diagnosis system in accordance with the present invention.

FIG. 1 is an explanatory view showing an X-ray image diagnosis system, which is an embodiment of the radiation image diagnosis system in accordance with the present invention. With reference to FIG. 1, the X-ray image diagnosis system comprises an X-ray producing device 1, an X-ray detector 2, an image processing unit 3, an imaging control device 4, a grid 5, and a grid detector 6. The X-ray producing device 1 and the X-ray detector 2 are located so as to stand facing each other with an object S intervening therebetween. Also, the imaging control device 4 is connected to the X-ray producing device 1, the X-ray detector 2, the image processing unit 3, and the grid detector 6. The X-ray detector 2 connected to the image processing unit 3.

The X-ray producing device 1 comprises an X-ray tube 11 for irradiating the X-rays and an X-ray high-voltage generator 12 for applying a tube voltage to the X-ray tube 11. The X-ray producing device 1 is controlled by the imaging control device 4 and is capable of successively irradiating the X-rays having different energy distributions. The X-rays having different energy distributions may be produced with a technique wherein the tube voltage is altered at the time of each irradiating operation and wherein the maximum value, the peak value, the mean value, or the like, on the X-ray spectral distribution is changed. Alternatively, the X-rays having different energy distributions may be produced with a technique wherein the X-rays having an identical energy distribution is produced and wherein the produced X-rays are caused to pass through one of filters having different characteristics at the time of each irradiating operation (reference may be made to, for example, U.S. Pat. No. 6,751,341). Also, the tube current and the irradiation time may be altered at the time of each irradiating operation, and the X-ray dose may thus be altered. The setting of the imaging conditions, such as the tube voltage, the tube current, the irradiation time, and the number of times of the irradiating operations, and the control of the operations in accordance with the imaging conditions having been set are performed by the imaging control device 4.

Figure 2:
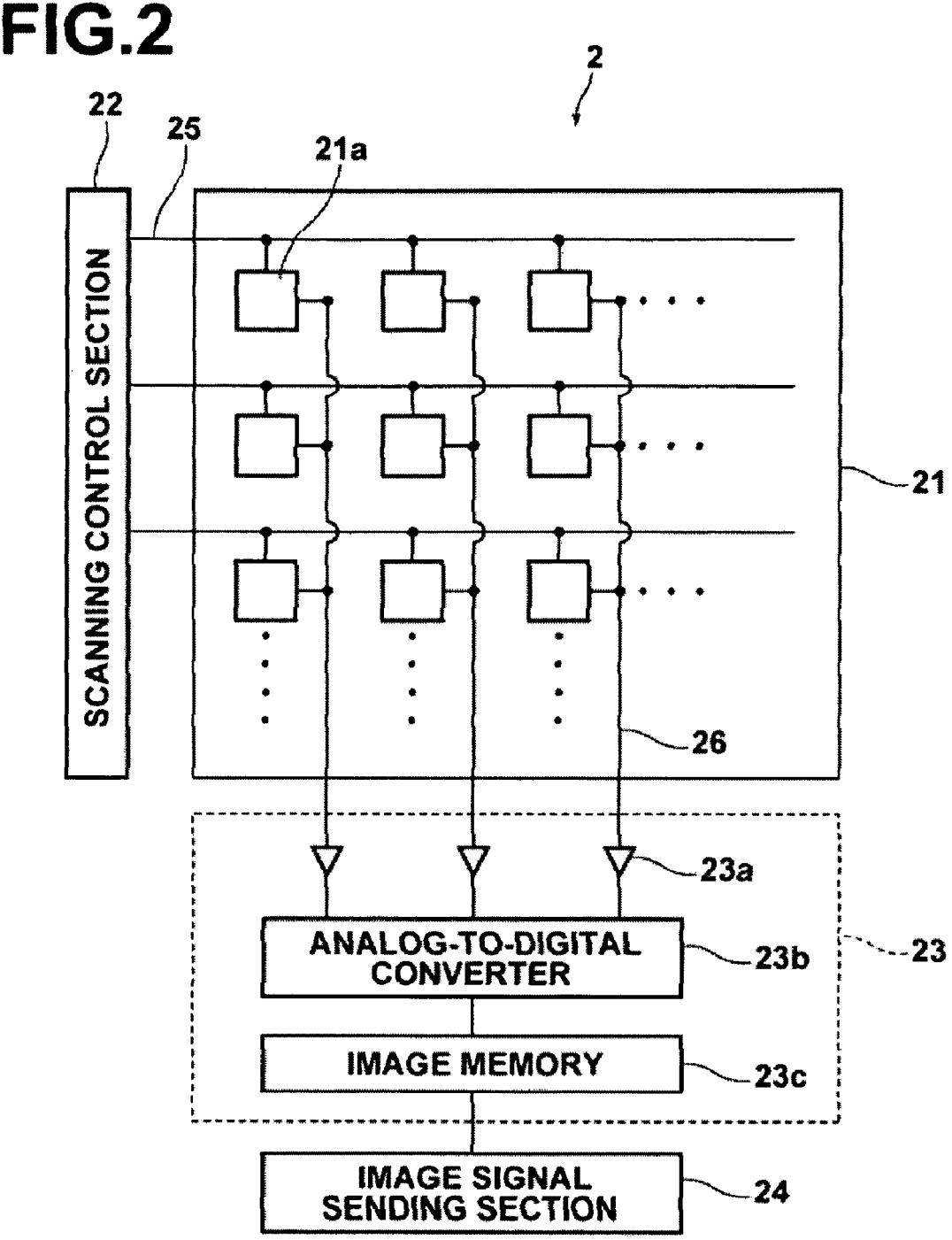
FIG. 2 is an explanatory view showing an X-ray detector.

The X-ray detector 2 is the flat panel type of detector (i.e., the flat panel detector: FPD). As illustrated in FIG. 2, the X-ray detector 2 comprises a detecting section 21. The detecting section 21 is constituted of an active matrix substrate and a plurality of detection elements 21a, 21a, . . . , which detect the X-rays, convert the X-rays into electric charges, and accumulate the electric charges. The plurality of detection elements 21a, 21a, . . . are located in a two-dimensional pattern on the active matrix substrate. The X-ray detector 2 also comprises a scanning control section 22 for controlling the timing with which the electric charges are read out from the detecting section 21. The X-ray detector 2 further comprises an image converting section 23 for reading out the electric charges having been accumulated at each of the detection elements 21a, 21a, . . . of the detecting section 21, performing logarithmic amplification of the electric charges, and thereafter performing the conversion into a digital image signal. The X-ray detector 2 still further comprises an image signal sending section 24 for sending the digital image signal to the image processing unit 3. The detection elements 21a, 21a, . . . arrayed along an identical row are connected by a common scanning signal line 25 to the scanning control section 22. Also, the detection elements 21a, 21a, . . . arrayed along an identical column are connected by a common image signal line 26 to the image converting section 24.

As each of the detection elements 21a, 21a, . . . , it is possible to employ a direct conversion type of detection element. With the direct conversion type of detection element, the X-rays are directly converted by a conversion layer containing amorphous selenium (a-Se), or the like, into electric charges in accordance with the incident dose, and the electric charges having been obtained from the conversion are accumulated at a capacitor connected to an electrode located under the conversion layer. Also, a gate side of a TFT switch is connected to the scanning signal line 25, a source side of the TFT switch is connected to the capacitor, and a drain side of the TFT switch is connected to the image signal line 26. When the TFT switch is turned on in accordance with the control signal sent from the scanning control section 22, an image signal component represented by the electric charges having been accumulated at the capacitor is outputted to the image signal line 26.

As each of the detection elements 21a, 21a, . . . , it is also possible to employ an indirect conversion type of detection element. With the indirect conversion type of detection element, the X-rays are converted by a fluorescent substance (i.e., a scintillator), such as cesium iodide (CsI), into light, and the light obtained from the conversion is converted by a photodiode into electric charges. The electric charges having thus been obtained from the conversion are accumulated at a capacitor. When the TFT switch having been connected in the same manner as that in the direct conversion type of detection element described above is turned on in accordance with the control signal sent from the scanning control section 22, the electric charges having been accumulated at the capacitor are outputted to the image signal line 26.

The scanning control section 22 is constituted as a gate circuit. The scanning control section 22 sends a pulsed signal to each of the scanning signal lines 25, 25, . . . with a predetermined timing in accordance with the control made by the imaging control device 4.

The image converting section 23 comprises a plurality of amplifiers 23a, 23a, . . . , each of which performs the logarithmic amplification on the image signal component having been outputted to the image signal line 26. The image converting section 23 also comprises an analog-to-digital converter 23b for digitizing the amplified image signal component. The image converting section 23 further comprises an image memory 23c for storing the digitized image signal component.

Also, the X-ray image diagnosis system is constituted such that the grid 5 may be loaded at a position between the object S and the X-ray detector 2 and may be unloaded from the loading position. The X-ray image diagnosis system is thus capable of performing the imaging operation with the grid and the imaging operation without the grid. Further, in the cases of the imaging operation with the grid, one of various kinds of grids (grids having various different grid ratios, grids having various different grid patterns, and the like) is capable of being used. The information representing the kind of the grid is recorded on a tag (a bar code) attached to the grid. This embodiment will hereinbelow be described by taking the cases, wherein one of the grids having different grid ratios is used selectively, as an example.

The grid detector 6 comprises a sensor for detecting the loading state or the unloading state of the grid 5. The grid detector 6 also comprises a reading section for reading the tag of the grid having been loaded. The grid detector 6 further comprises a communication section for sending the information (hereinbelow referred to as the grid information), which represents the presence or absence of the grid having been detected by the sensor, and the grid ratio having been read by the reading section, to the imaging control section 4.

The image processing unit 3 is constituted of a computer provided with a high definition liquid crystal display device for displaying images, and the like, a keyboard, a mouse device, and the like, from which instructions are inputted by the user, and a main body comprising a CPU, a memory, a hard disk, a communication interface, and the like. The image processing unit 3 has the functions for forming the constituent images by performing the energy subtraction processing.

Figure 3:
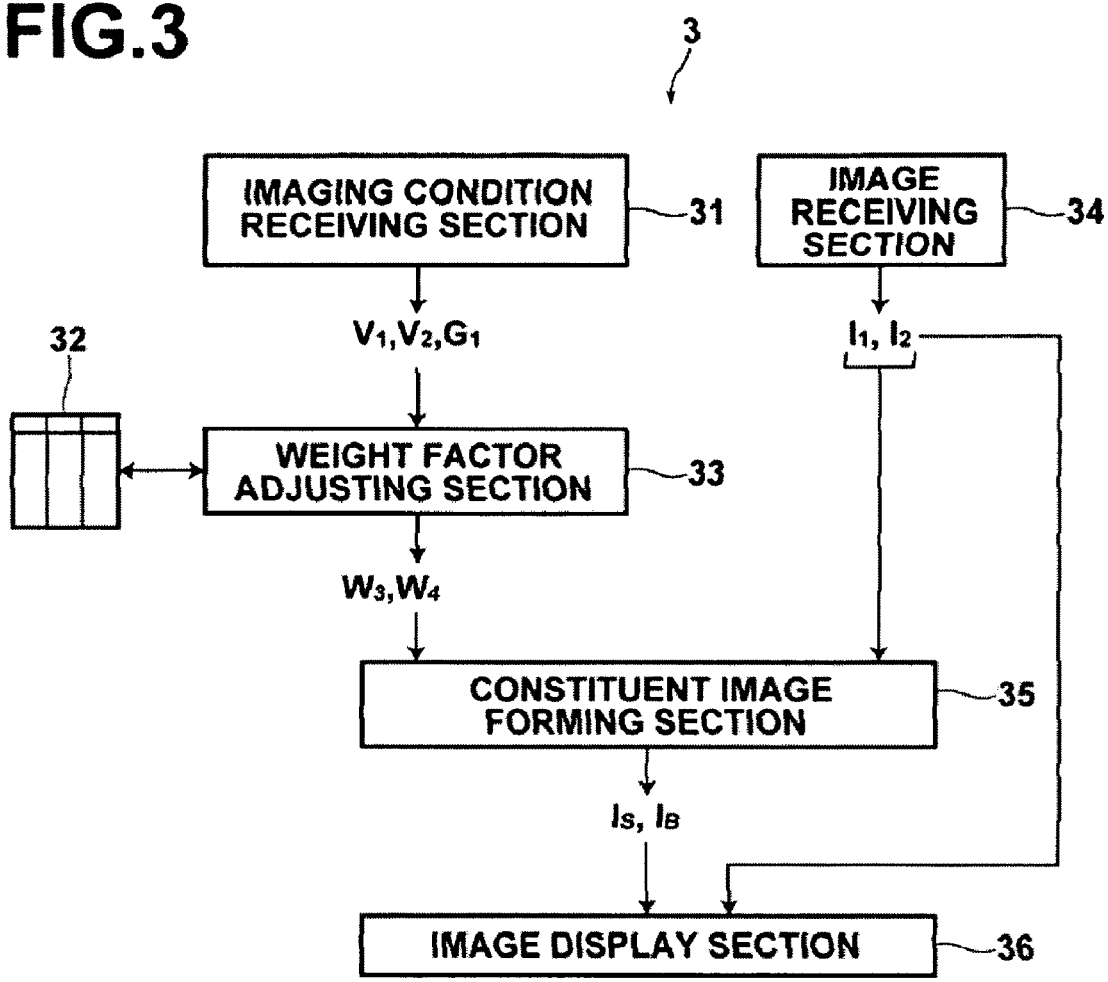
FIG. 3 is a block diagram showing a constitution for performing energy subtraction processing in an image processing unit.

As illustrated in FIG. 3, the image processing unit 3 comprises an imaging condition receiving section 31 for acquiring the information, which represents the imaging conditions, from the imaging control device 4. The image processing unit 3 also comprises a weight factor adjusting section 33 for making reference to a weight factor table 32 in accordance with the received information, which represents the imaging conditions, and acquiring the weight factors for each of the constituent images to be separated and for each of the images. The image processing unit 3 further comprises an image receiving section 34 for receiving the image signals representing the two images having been sent from the X-ray detector 2. The image processing unit 3 still further comprises a constituent image forming section 35 for performing the weighted subtraction process on corresponding pixels in the two received images by use of the weight factors, which have been adjusted by the weight factor adjusting section 33, and thereby forming two constituent images representing the constituents in the object. The image processing unit 3 also comprises an image display section 36 for displaying the constituent images having been formed, and the diagnostic image having been received from the image receiving section 34.

The energy subtraction processing is performed through the execution of a computer program having been stored in the image processing unit 3. The computer program may be installed in the image processing unit 3 from a computer readable recording medium, such as a CD-ROM. Alternatively, the computer program may be down-loaded from a server, which is connected via a network, such as an internet, and may then be installed in the image processing unit 3.

The information representing the imaging conditions, which information is acquired by the imaging condition receiving section 31, contains the tube voltage at the time of the imaging operation, whether the grid is used or is not used, and the grid ratio in cases where the grid is used.

Figures 4, 5:
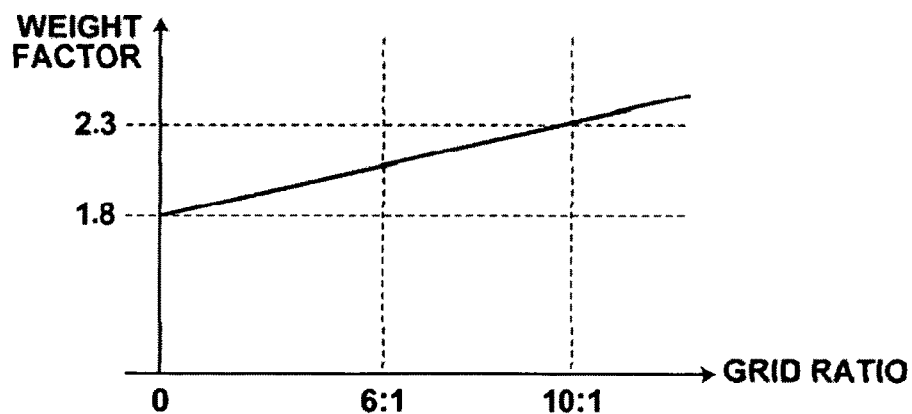
FIG. 4 is a diagram showing an example of a weight factor table.
FIG. 5 is a graph showing an example of relationship between a grid ratio and a weight factor.

As exemplified in FIG. 4, the weight factor table 32 represents the correspondence relationship between each of combinations of the information, which represents the imaging conditions, with the constituent, which is to be separated, and the weight factor for each of the two radiation images. Specifically, the weight factor table 32 specifies the value of the weight factor for the extraction of the constituent, which is to be separated, from the inputted radiation images with respect to each of the tube voltage, which is set at the time of the imaging operation performed for each of the inputted radiation images, the grid information, and the constituent, which is to be separated. In the example illustrated in FIG. 4, the information, which represents the imaging conditions, contains the tube voltage, which represents the energy distribution at the time of each of the two times of irradiation, and the grid information obtained by the grid detector 6. As the tube voltages, the low voltage and the high voltage are illustrated in this order. As shown above in Formulas (9) and (11), the weight factor represents the value of the weight factor for the image (hereinbelow referred to as the high-energy image), which is recorded with the high tube voltage, in cases where the weight factor for the image (hereinbelow referred to as the low-energy image), which is recorded with the low tube voltage, is taken as 1. The registration of the values in the table may be performed in accordance with data on results of experiments having been performed previously.

Figure 6:
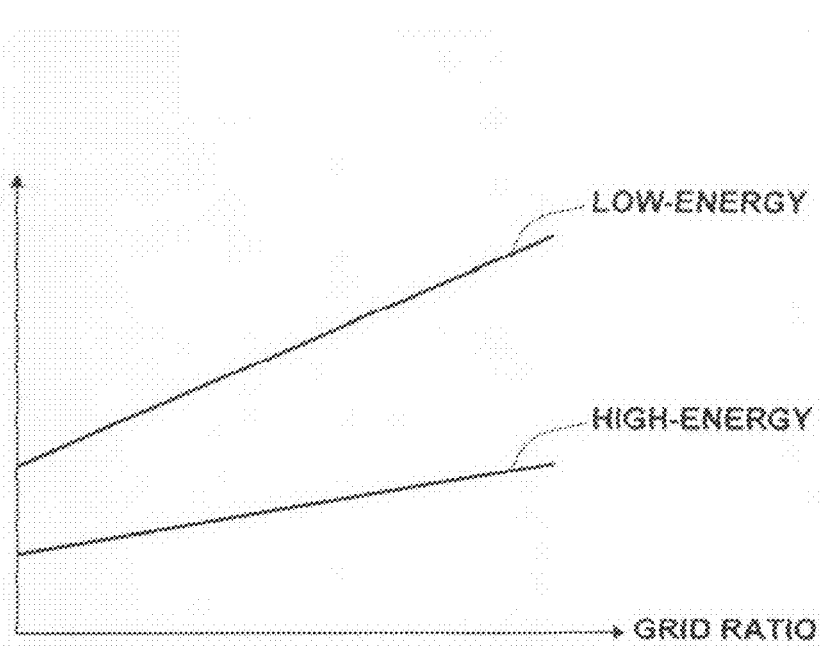
FIG. 6 is a graph showing an example of relationship between a grid ratio and a radiation attenuation coefficient of each of X-ray images having different energy distributions.

FIG. 5 is a graph showing an example of relationship between a grid ratio and a weight factor for erasing a bone image and forming a soft tissue image in cases where imaging operations are performed at a tube voltage of 60 kVp and a tube voltage of 120 kVp. As shown above in Formula (9), the weight factor represents the value of the weight factor for the high-energy image in cases where the weight factor for the low-energy image is taken as 1. Also, a grid ratio of 0 represents that the grid is not used. Ordinarily, the low-energy radiation is apt to be absorbed more readily by a substance than the high-energy radiation. Therefore, in cases where the grid is used at the time of the imaging operation, the quantity of the radiation absorbed by the grid becomes larger in the cases of the imaging operation performed with the low-energy radiation than in the cases of the imaging operation performed with the high-energy radiation. Thus the scattered radiation removing effect becomes larger in the cases of the imaging operation performed with the low-energy radiation than in the cases of the imaging operation performed with the high-energy radiation. Accordingly, as illustrated in FIG. 6, the increase rate of the absolute value of the radiation attenuation coefficient, which increase rate is obtained by the use of the grid, is higher in the cases of the low-energy image than in the cases of the high-energy image. Also, as the grid ratio becomes high, the scattered radiation removing effect becomes large. Therefore, the increase rate of the absolute value of the radiation attenuation coefficient, which increase rate accompanies the increase of the grid ratio, is higher in the cases of the low-energy image than in the cases of the high-energy image. Accordingly, the increase rate of the numerator in Formula (9) shown above becomes higher than the increase rate of the denominator in Formula (9) shown above, and the relationship between the weight factor and the grid ratio as illustrated in FIG. 5 is obtained.

Figure 7:
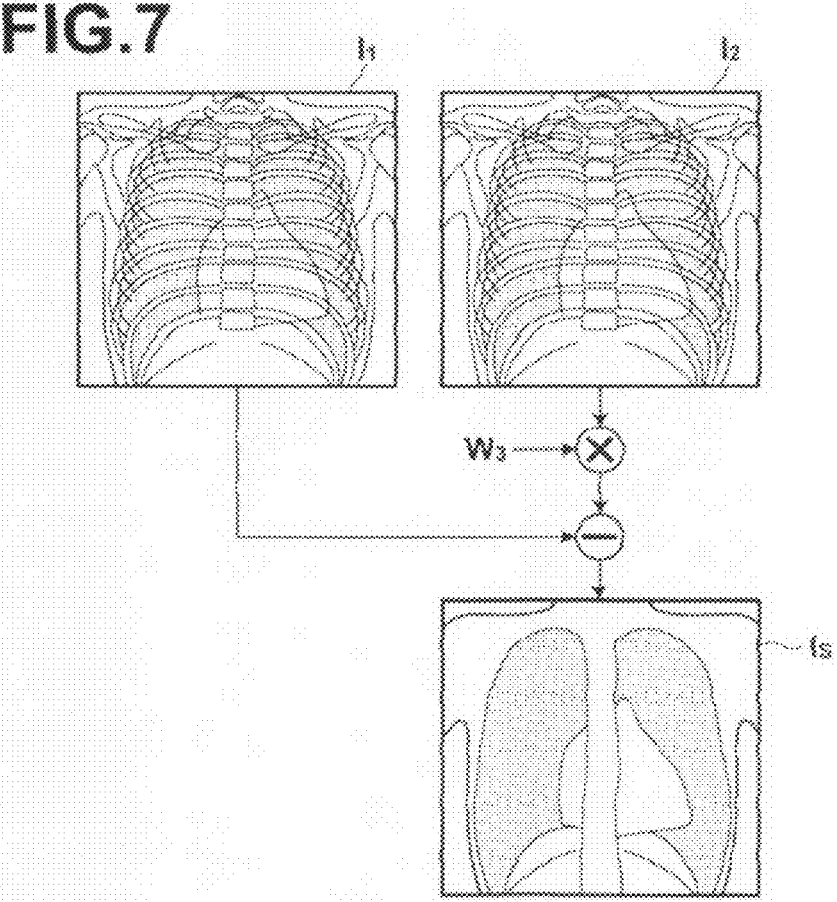
FIG. 7 is an explanatory view showing how a soft tissue image is formed with energy subtraction processing.
Figure 8:
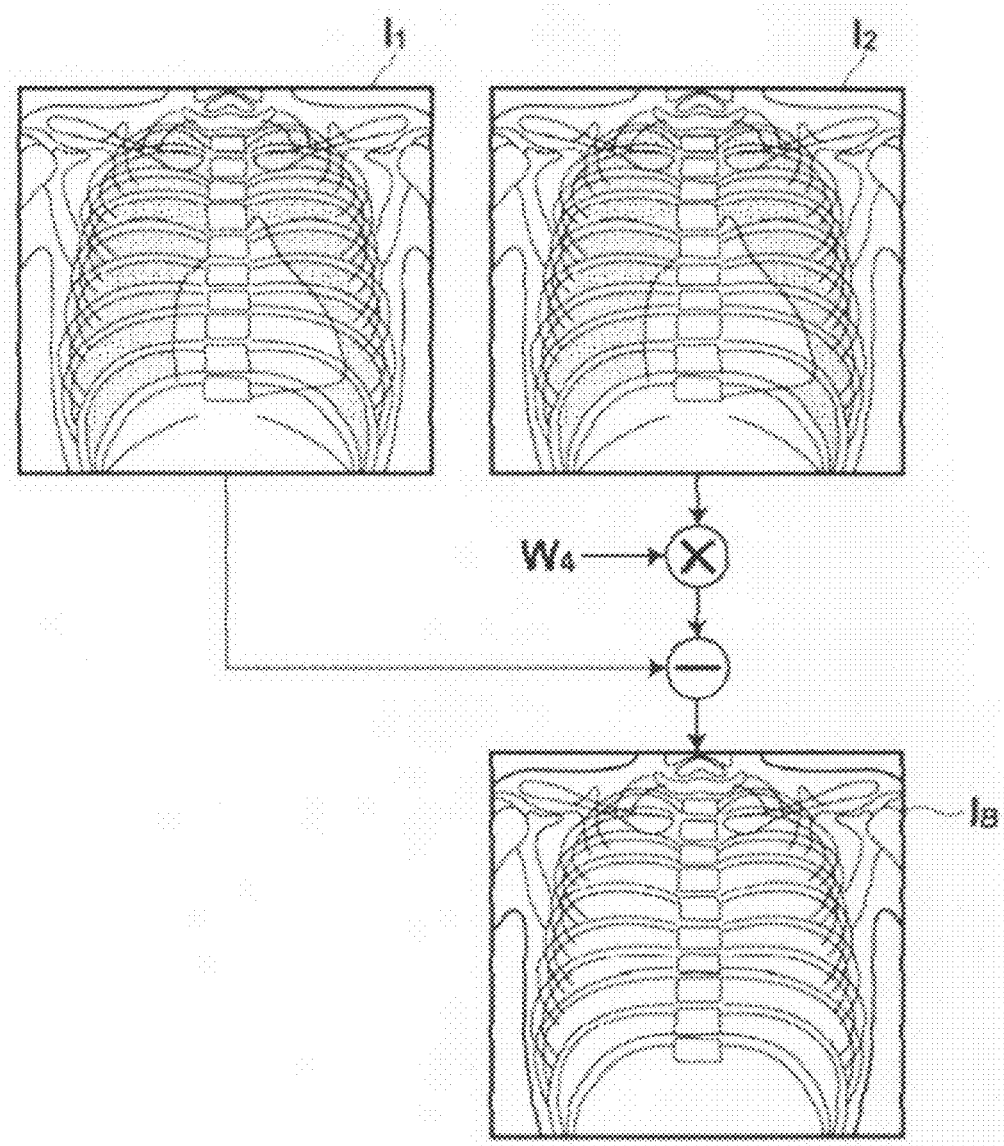
FIG. 8 is an explanatory view showing how a bone image is formed with energy subtraction processing.

FIG. 7 is an explanatory view showing how a soft tissue image is formed with energy subtraction processing performed by a constituent image forming section 35. FIG. 8 is an explanatory view showing how a bone image is formed with energy subtraction processing performed by the constituent image forming section 35. In the examples, as illustrated in FIG. 3, the tube voltage for an input image $I_1$ is represented by $V_1$, and the tube voltage for an input image $I_2$ is represented by $V_2$ ($V_1<V_2$). Also, the grid ratio of the grid at the time of each of the imaging operations is represented by $G_1$. Further, as a result of reference made by the weight factor adjusting section 33 to the weight factor table 32 illustrate in FIG. 4, the weight factor for the image $I_2$ is adjusted to be $w_3$ in cases where the constituent image to be separated is the soft tissue image, and the weight factor for the image $I_2$ is adjusted to be $w_4$ in cases where the constituent image to be separated is the bone image (the weight factor for the image $I_1$ recorded at the tube voltage $V_1$ is taken as 1). Firstly, as illustrated in FIG. 7, the weighted subtraction process represented by the formula of $I_1-w_3 \cdot I_2$ is performed on the corresponding pixels in the input images $I_1$ and $I_2$ containing the soft tissue constituent and the bone constituent. With the weighted subtraction process, a soft tissue image $I_s$, from which the bone constituent has been removed, is formed. Also, as illustrated in FIG. 8, the weighted subtraction process represented by the formula of $I_1-w_4 \cdot I_2$ is performed on the corresponding pixels in the input images $I_1$ and $I_2$ containing the soft tissue constituent and the bone constituent. With the weighted subtraction process, a bone image $I_B$, from which the soft tissue constituent has been removed, is formed. The corresponding pixels in the X-ray images may be specified with operations, wherein a set of pixels which correspond spatially with each other are obtained by taking a predetermined structure (an object site, the image of which is to be seen, a marker pattern, or the like) in each of the X-ray images as a reference. For example, in the cases of the images having been obtained with an imaging technique such that the position of the predetermined structure in each of the images may not deviate between the images, the pixels whose spatial coordinates on the spatial coordinate systems of the respective images coincide with each other may be obtained as the aforesaid corresponding pixels in the X-ray images. In the cases of the images having been obtained with an imaging technique such that a shift occurs between the images, it is preferable to perform linear position matching processing with image size enlargement or reduction processing, parallel translation, rotating processing, and the like; nonlinear position matching processing with strain transform, or the like; or position matching processing in which the linear position matching processing and the nonlinear position matching processing are combined with each other. For the position matching between the images, it is also possible to employ a technique described in, for example, U.S. Pat. No. 6,751,341, or one of techniques which will be known at the time of execution of the present invention.

Figure 9:
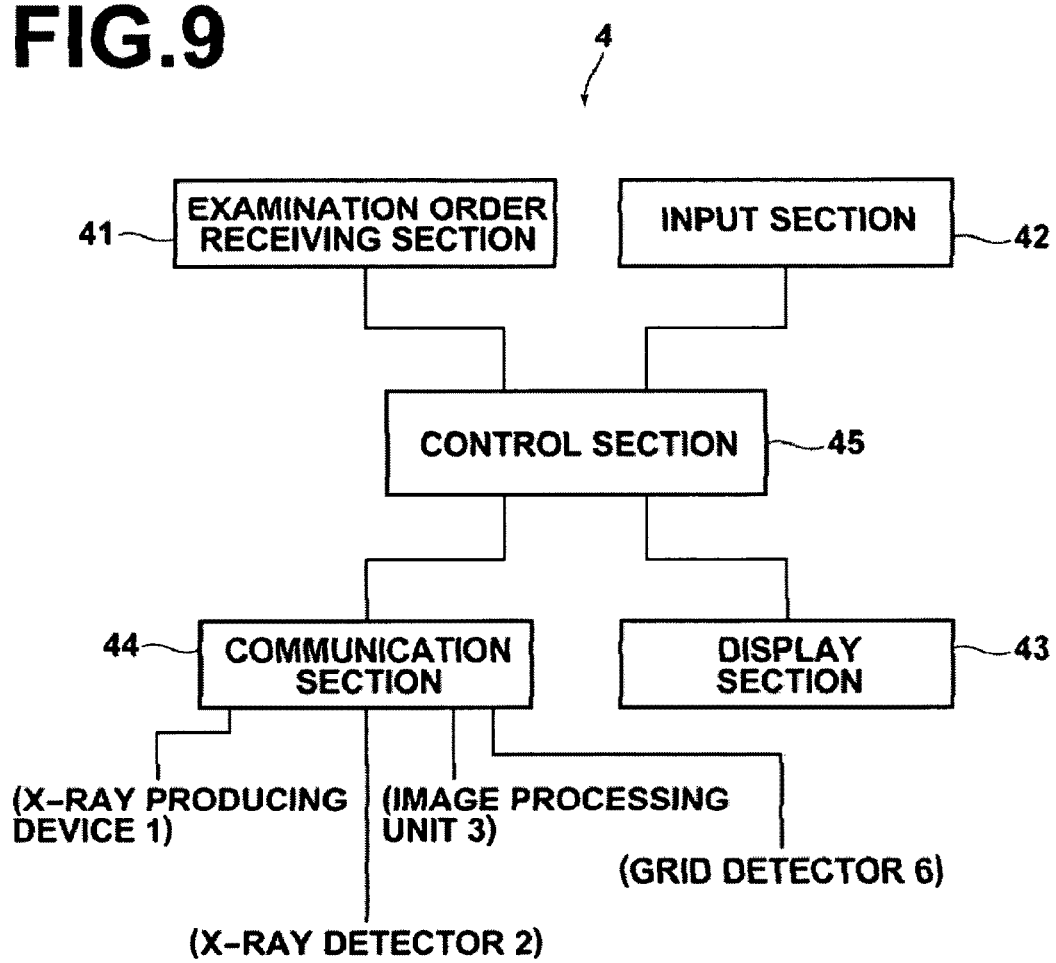
FIG. 9 is an explanatory view showing a constitution of an imaging control device.

With reference to FIG. 9, the imaging control device 4 comprises an examination order receiving section 41 for receiving examination order information from an ordering system, which issues examination orders containing the order for the imaging operation for image diagnosis and the order for image formation. The imaging control device 4 also comprises an input section 42 provided with a touch panel, or the like, from which the instructions are inputted by the user. The imaging control device 4 further comprises a display section 43 for displaying various kinds of information representing the examination orders, the imaging conditions, and the like. The imaging control device 4 still further comprises a communication section 44 for performing the sending and receiving of signals, which represent the imaging conditions, and operation control signals with respect to the X-ray producing device 1, the X-ray detector 2, the image processing unit 3, and the grid detector 6. The imaging control device 4 also comprises a control section 45 for controlling the operations of the respective sections in accordance with the examination order information, which has been received by the examination order receiving section 41, and the information, which has been inputted from the input section 42. In this embodiment, the input of the information representing the tube voltage at the time of the imaging operation is made from the input section 42. Also, in cases where the grid 5 is loaded, the grid information sent from the grid detector 6 is received by the communication section 44. Further, the control section 45 sends the information representing the tube voltage, which information has been inputted from the input section 42, and the grid information, which has been received by the communication section 44, to the image processing unit 3 via the communication section 44.

Figure 10:
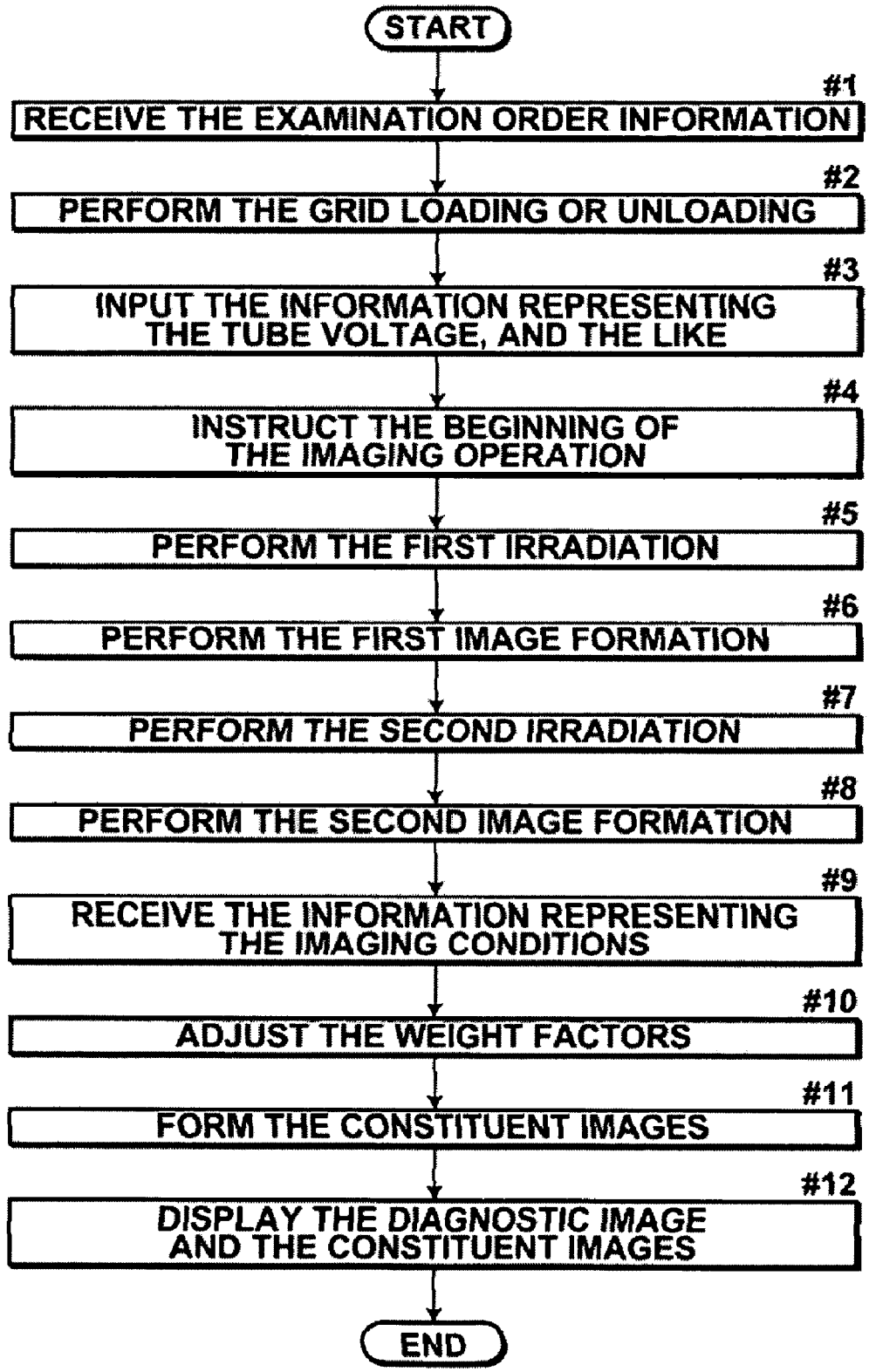
FIG. 10 is a flow chart showing a flow of processes performed by the embodiment of the X-ray image diagnosis system in accordance with the present invention.
Figure 12:
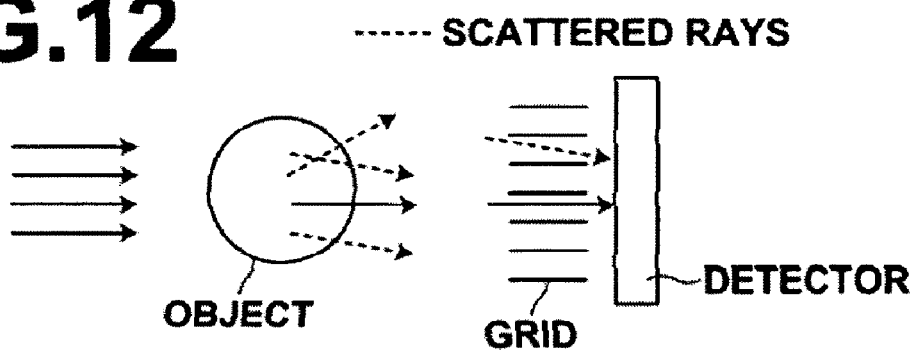
FIG. 12 is an explanatory view showing a scattered radiation removing effect of a grid.
Figure 13:
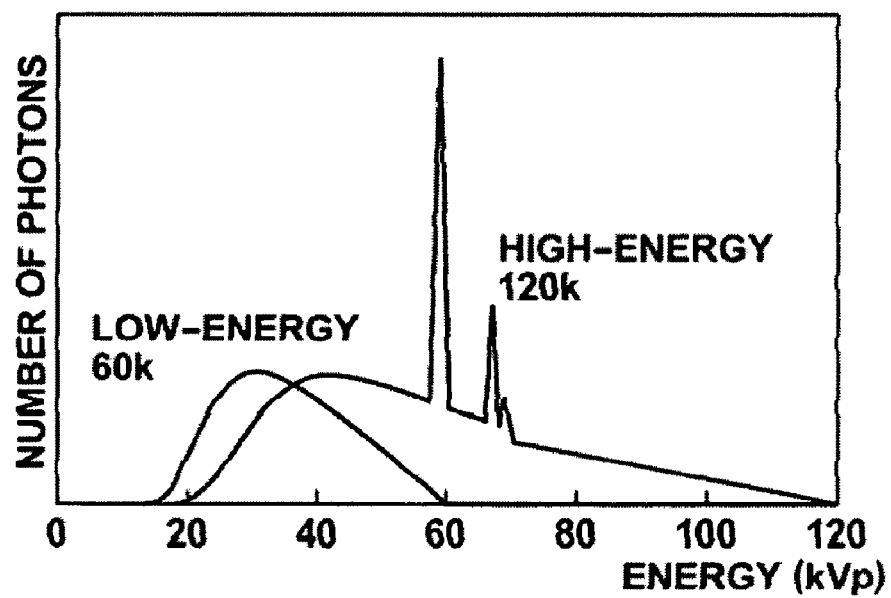
FIG. 13 is a graph showing examples of spectral distributions of two kinds of radiation having different energy distributions (low-energy radiation and high-energy radiation)
Figures 14, 15:
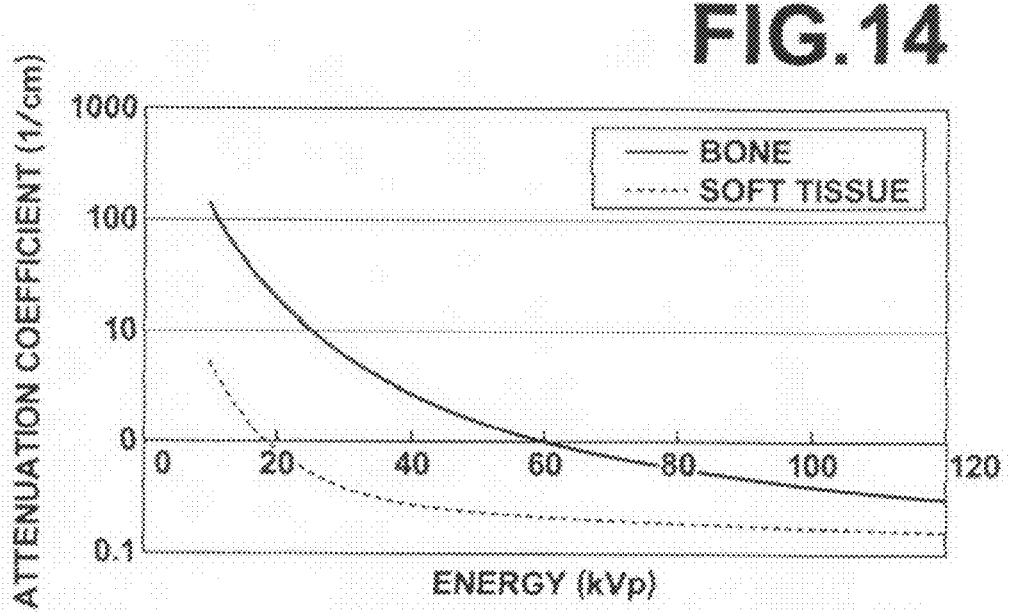
FIG. 14 is a graph showing examples of relationships between radiation attenuation coefficients of a bone and a soft tissue of a human body and a tube voltage of a radiation producing device.
FIG. 15 is an explanatory sectional view showing a grid.

FIG. 10 is a flow chart showing a flow of processes performed by the embodiment of the X-ray image diagnosis system in accordance with the present invention.

Firstly, as stages for preparation for the imaging operations, a step #1, a step #2, and a step #3 described below are performed. Specifically, in the step #1, the examination order receiving section 41 of the imaging control device 4 receives the examination order information, which represents an order for acquiring a diagnostic image, a bone image, and a soft tissue image with general imaging operations on the frontal chest by use of the two-shot energy subtraction processing technique. The control section 45 controls the display section 43 so as to display the contents of the received examination order. Thereafter, in the step #2, the radiation engineer acting as the user makes the adjustments as to whether the grid is to be used or is not to be used at the time of the imaging operations, and as to the grid ratio in accordance with the contents of the examination order and performs the loading or unloading of the grid 5. Also, the grid detector 6 detects the state of the grid loading or unloading. In cases where the grid has been unloaded, the grid detector 6 sends the information, which represents that the grid is not used, to the imaging control device 4. In cases where the grid has been loaded, the grid detector 6 reads out the grid information and sends the thus read-out grid information to the imaging control device 4. Further, in the step #3, the radiation engineer adjusts the number of times of the X-ray irradiation operations, the tube voltage for each X-ray irradiation operation, the tube current for each X-ray irradiation operation, and the irradiation time for each X-ray irradiation operation in accordance with the contents of the examination order and inputs the information representing the thus adjusted conditions from the input section 42 of the imaging control device 4. Of the inputted information, which represents the tube voltage, the tube current, and the exposure time, the information concerning the first irradiation operation is sent via the communication section 44 to the X-ray producing device 1 and the X-ray detector 2. Pre-processing for the imaging operation is performed in each of the devices, and the preparations for the imaging operation are completed. At this time, a response signal representing the completion of the preparations for the imaging operation is sent from each of the devices to the imaging control device 4. The control section 45 of the imaging control device 4 detects the completion of the preparations for the imaging operation in each of the devices and controls the display section 43 so as to display a message representing that the imaging operation is capable of being begun.

In a step #4, the radiation engineer confirms that the imaging operation is capable of being begun. Also, the radiation engineer confirms the posture of the object S, and the like, and makes an instruction for the beginning of the imaging operation from the input section 42. Thereafter, in a step #5, the control section 45 having accepted the instruction for the beginning of the imaging operation turns on an irradiation signal and sends the irradiation signal via the communication section 44 to the X-ray producing device 1. In the X-ray producing device 1 having received the irradiation signal, the X-ray high-voltage generator 12 applies energy to the X-ray tube 11, and the first X-ray irradiation operation from the X-ray tube 11 is begun. In the imaging control device 4, the control section 45 monitors whether the irradiation time having been set has or has not elapsed. At the time at which the irradiation time having been set has elapsed, the control section 45 turns off the irradiation signal and sends the turning-off signal to the X-ray producing device 1. In the X-ray producing device 1 having received the turning-off signal, the X-ray high-voltage generator 12 ceases the energy application to the X-ray tube 11, and the first X-ray irradiation operation from the X-ray tube 11 is thus finished. Thereafter in a step #6, in the imaging control device 4, the control section 45 sends information, which instructs the first electric charge reading operation, to the X-ray detector 2. In the X-ray detector 2 having received the information, which instructs the first electric charge reading operation, the scanning control section 22 sends the control signal to the scanning signal lines 25, 25, . . . successively, and the electric charges having been accumulated at the detection elements 21a, 21a, . . . are successively read out. The electric charges having been read out are subjected to the amplification and the analog-to-digital conversion and stored in the image memory 23c. At the time at which the readout of the electric charges from all of the detection elements 21a, 21a, . . . has been finished, the image signal sending section 24 sends the image signal representing the radiation image having been obtained with the first irradiation operation, which image signal has been stored in the image memory 23c, to the image processing unit 3. Also, after the pre-processing for the detection of the X-rays with the second irradiation operation has been performed, the X-ray detector 2 sends a response signal, which represents the completion of the preparations for the second irradiation operation, to the imaging control device 4.

At the same time as the aforesaid sending of the information, which instructs the first electric charge reading operation, to the X-ray detector 2, the imaging control device 4 sends the information, which represents the tube voltage and the tube current in the second irradiation operation, via the communication section 44 to the X-ray producing device 1. The X-ray producing device 1 receives the information concerning the second irradiation operation, performs the pre-processing for the second irradiation operation, and sends the response signal, which represents the completion of the preparations for the second irradiation operation, to the imaging control device 4.

The control section 45 of the imaging control device 4 receives the response signals from the X-ray producing device 1 and the X-ray detector 2 via the communication section 44. Thereafter, in a step #7, in the same manner as that in the step #5, the second X-ray irradiation operation is performed. Also, in a step #8, in the same manner as that in the step #6, the X-ray image is formed with the second irradiation operation.

Also, the control section 45 of the imaging control device 4 sends the information, which represents the imaging conditions (the tube voltage and the grid information) in the two times of the imaging operations, via the communication section 44 to the image processing unit 3.

In the step #6 and the step #8, in the image processing unit 3, the image receiving section 34 receives the image signals $I_1$ and $I_2$ representing the radiation images, each of which has been obtained with one of the two irradiation operations, and stores each of the image signals $I_1$ and $I_2$ in one of different memory regions. Also, in a step #9, the imaging condition receiving section 31 receives the information, which represents the imaging conditions and has been sent from the imaging control device 4. Thereafter, in a step #10, the weight factor adjusting section 33 makes reference to the weight factor table 32 by use of the received imaging conditions as a retrieval key and acquires the weight factors $w_3$ and $w_4$ for the image $I_2$, which has been obtained with the X-rays produced by the higher tube voltage between the two images having been formed with the imaging operations described above. Also, in a step #11, the constituent image forming section 35 forms the soft tissue image $I_s$ with the weighted subtraction process represented by the formula of $I_1 - w_3 \cdot I_2$ and forms the bone image $I_B$ with the weighted subtraction process represented by the formula of $I_1 - w_4 \cdot I_2$. Further, in a step #12, the image display section 36 displays the high-energy image $I_2$ for diagnosis, the soft tissue image $I_s$, and the bone image $I_B$ on the display screen.

As described above, in this embodiment, the imaging condition receiving section 31 acquires the information, which represents the tube voltages in the imaging operations for the two X-ray images, and the grid information, which represents the grid use conditions in the imaging operations for the two X-ray images. Also, the weight factor adjusting section 33 makes reference to the weight factor table 32 and adjusts the weight factors in accordance with the tube voltage and the grid information. Therefore, the weight factors are adjusted such that the weight factors accurately reflect the tube voltage and the grid use conditions at the time of the imaging operations. Further, the constituent image forming section 35 performs the weighted subtraction process by use of the thus adjusted weight factors, and therefore the constituent images are obtained accurately.

In the embodiment described above, the grid ratio is employed as the grid information. It is also possible to employ other kinds of information concerning the grid, such as the grid information representing the grid density, the grid information representing the grid pattern (the linear grid, the cross grid), and the grid information representing the grid material. In such cases, the grid information may be recorded on the tag of the grid 5 and may be read out by the grid detector 6, and the imaging control device 4 may send the grid information to the image processing unit 3. Also, in the weight factor table 32 of the image processing unit 3, the value of the weight factor may be registered with respect to each of the tube voltage, the other kinds of grid information, and the constituent, which is to be separated.

Further, in the embodiment described above, the imaging condition receiving section 31 receives the information, which represents the tube voltages in the imaging operations for the two X-ray images, and the grid information, which represents the grid use conditions in the imaging operations for the two X-ray images, from the imaging control device 4. Alternatively, in lieu of the aforesaid information being received by the imaging condition receiving section 31, the image processing unit 3 may receive the examination order information, and the weight factor may be adjusted in accordance with the examination order information. Specifically, as exemplified in FIG. 11, there may be prepared a reference table defining the tube voltages in the imaging operations for the two X-ray images, and the grid information, which represents the grid use conditions in the imaging operations for the two X-ray images, with respect to each of the objects sites, the images of which are to be recorded. Also, the image processing unit 3 may receive the examination order information, and the weight factor adjusting section 33 may make reference to the reference table of FIG. 11 by use of the information representing the object site to be imaged, which information is contained in the examination order information, as the retrieval key and may thus acquire the information representing the tube voltage and the grid information in accordance with the object site to be imaged. Further, the weight factor adjusting section 33 may make reference to the weight factor table 32 by use of the thus acquired information representing the tube voltage and the thus acquired grid information as the retrieval key and may thereby acquire the weight factor fully satisfying the conditions with the retrieval key. One of the two images obtained from the imaging operations for the energy subtraction processing should preferably be recorded under the conditions identical with the conditions for the ordinary diagnosis. In such cases, at the time of the energy subtraction processing, it is sufficient for only one additional image to be recorded besides the image for the ordinary diagnosis. Therefore, the advantages are obtained in that the radiation dose to the patient may not become markedly large. Accordingly, the reference table of FIG. 11 also defines which image between the two X-ray images is to be used as the diagnostic image. The reference table of FIG. 11 may also be used for the selection of the diagnostic image to be displayed by the image display section 36. For example, in cases where the object site to be imaged is the chest, the high-energy image is used as the diagnostic image. In cases where the object site to be imaged is the abdomen, the low-energy image is used as the diagnostic image.

The weight factor table 32 illustrated in FIG. 4 has been set as an example. The relationships among the tube voltage, the grid information, and the weight factor may be obtained previously from experiments with respect to each of grids, which will be used in the X-ray image diagnosis system and registered in the weight factor table 32. By use of the weight factor table 32, in every case where a grid having specific characteristics is used, the weight factor adjusting section 33 is capable of adjust the optimum weight factor in accordance with the use conditions of the grid.

The present invention may be embodied in various other ways with respect to the system constitution, the reference table constitution, the processing flow, or the like. The embodiment described above is intended to illustrate an example, and the foregoing descriptions are not to be construed to limit the technical scope of the invention.

For example, in the embodiment described above, the X-ray images obtained from the imaging operations with the two-shot energy subtraction processing technique are used. However, the prevent invention is applicable also to images obtained with the one-shot energy subtraction processing technique.

Also, in the embodiment described above, the two kinds of the constituent images are formed from the two X-ray images. However, the present invention is applicable also to the processing, wherein at most N kinds of constituent images are formed from N number of X-ray images (where N=2, 3, 4, . .

.). In such cases, for example, the weight factor for each of the N number of inputted X-ray images may be defined in the weight factor table 32 with respect to each of the tube voltage, the grid information, and the constituent, which is to be separated.

Further, as the X-ray detector 2, in lieu of the flat panel type detector being used, a stimulable phosphor sheet provided with a sheet-shaped stimulable phosphor layer may be used. In such cases, the radiation image information of the object is stored on the stimulable phosphor sheet, and the stimulable phosphor sheet on which the radiation image information has been stored is exposed to stimulating rays, such as a laser beam, which cause the stimulable phosphor sheet to emit light in proportion to the stored radiation image information. The light emitted from the stimulable phosphor sheet is detected photoelectrically, and an analog image signal is thereby acquired. The analog image signal is then subjected to the logarithmic conversion and digitization, and a digital image signal is thus formed.

Furthermore, the grid 5 may be a stationary grid or a movable grid.

Also, in the embodiment described above, the processing is performed on the assumption that, after the image signal having been read out is subjected to the logarithmic conversion performed by the amplifiers 23a, 23a, . . . , the digital image signal is formed. Therefore, the process for forming the constituent image by the constituent image forming section 35 is referred to as the "weighted addition or subtraction process". In cases where the constituent image is to be separated from the image having not been subjected to the logarithmic conversion, the term "sum" as used herein may be replaced by the term "product", and the term "difference" may be replaced by the term "quotient". In such cases, the same effects as those described above are obtained.

What is claimed is:

1. An energy subtraction processing apparatus, comprising constituent image forming means for:
    receiving input of a plurality of radiation images having been formed with radiation carrying image information of an object, each of the radiation images representing degrees of transit attenuation of one of a plurality of patterns of radiation having different energy distributions, which transit attenuation occurs in the object,
    performing a weighted addition or subtraction process on corresponding pixels in the plurality of the radiation images by use of given weight factors, and
    thereby forming a constituent image representing a predetermined constituent in the object,
    wherein the apparatus further comprises:
    grid information acquiring means for acquiring grid information representing grid use conditions at the time of the imaging operations for the plurality of the radiation images, and
    weight factor adjusting means for adjusting the weight factors in accordance with the grid information, which has been acquired by the grid information acquiring means,
    the constituent image forming means performing the weighted addition or subtraction process by use of the weight factors, which have been adjusted by the weight factor adjusting means.

2. An energy subtraction processing apparatus as defined in claim 1 wherein the grid information is the information, which represents whether the grid is used or is not used at the time of the imaging operation, and/or the information, which represents the kind of the grid used at the time of the imaging operation.

3. An energy subtraction processing apparatus as defined in claim 1 wherein the grid information is the information, which represents whether the grid is used or is not used at the time of the imaging operation, and
    the weight factor adjusting means adjusts the weight factors such that an increase rate of an absolute value of the weight factor for a radiation image representing the degrees of transit attenuation of radiation having an energy distribution on a higher-energy side among the plurality of the radiation images, which absolute value is set in cases where the grid is used at the time of the imaging operation, with respect to the absolute value of the weight factor for the radiation image representing the degrees of transit attenuation of the radiation having the energy distribution on the higher-energy side among the plurality of the radiation images, which absolute value is set in cases where the grid is not used at the time of the imaging operation, is higher than the increase rate of the absolute value of the weight factor for a radiation image representing the degrees of transit attenuation of radiation having an energy distribution on a lower-energy side among the plurality of the radiation images, which absolute value is set in cases where the grid is used at the time of the imaging operation, with respect to the absolute value of the weight factor for the radiation image representing the degrees of transit attenuation of the radiation having the energy distribution on the lower-energy side among the plurality of the radiation images, which absolute value is set in cases where the grid is not used at the time of the imaging operation.

4. An energy subtraction processing apparatus as defined in claim 1 wherein the grid information contains the information, which represents a grid ratio of the grid used at the time of the imaging operation, and
    the weight factor adjusting means adjusts the weight factors such that an increase rate of an absolute value of the weight factor for a radiation image representing the degrees of transit attenuation of radiation having an energy distribution on a higher-energy side among the plurality of the radiation images, which increase rate accompanies an increase of the grid ratio, is higher than the increase rate of the absolute value of the weight factor for a radiation image representing the degrees of transit attenuation of radiation having an energy distribution on a lower-energy side among the plurality of the radiation images, which increase rate accompanies the increase of the grid ratio.

5. A radiation image diagnosis system, comprising:
    i) radiation irradiating means for irradiating radiation having a predetermined energy distribution to an object,
    ii) radiation detecting means for detecting the irradiated radiation,
    iii) conversion means for converting the detected radiation into a digital image signal and thereby forming the digital image signal representing a radiation image of the object, and
    iv) constituent image forming means for:
    receiving input of a plurality of digital image signals, each of which has been formed by the conversion means and represents one of a plurality of radiation images having been formed with radiation carrying image information of an object, each of the radiation images representing degrees of transit attenuation of one of a plurality of patterns of radiation having different energy distributions, which transit attenuation occurs in the object, performing a weighted addition or subtraction process on corresponding pixels in the plurality of the radiation images by use of given weight factors, and thereby forming a constituent image representing a predetermined constituent in the object, wherein the system is constituted such that a given grid may be located between the object and the radiation detecting means, and the system further comprises:

grid information acquiring means for acquiring grid information representing grid use conditions at the time of the imaging operations for the plurality of the radiation images, and weight factor adjusting means for adjusting the weight factors in accordance with the grid information, which has been acquired by the grid information acquiring means, the constituent image forming means performing the weighted addition or subtraction process by use of the weight factors, which have been adjusted by the weight factor adjusting means.

6. An energy subtraction processing method, comprising a constituent image forming step of:

receiving input of a plurality of radiation images having been formed with radiation carrying image information of an object, each of the radiation images representing degrees of transit attenuation of one of a plurality of patterns of radiation having different energy distributions, which transit attenuation occurs in the object, performing a weighted addition or subtraction process on corresponding pixels in the plurality of the radiation images by use of given weight factors, and thereby forming a constituent image representing a predetermined constituent in the object, wherein the method further comprises:

a grid information acquiring step of acquiring grid information representing grid use conditions at the time of the imaging operations for the plurality of the radiation images, and a weight factor adjusting step of adjusting the weight factors in accordance with the grid information, which has been acquired, the constituent image forming step being the step of performing the weighted addition or subtraction process by use of the weight factors, which have been adjusted by the weight factor adjusting step.

* * * * *